United States Patent
Jeong et al.

(10) Patent No.: US 9,606,065 B2
(45) Date of Patent: Mar. 28, 2017

(54) QUANTITATIVE ANALYSIS METHOD FOR MEASURING TARGET ELEMENT IN SPECIMEN USING LASER-INDUCED PLASMA SPECTRUM

(71) Applicant: GWANGJU INSTITUTE OF SCIENCE AND TECHNOLOGY, Gwangju (KR)

(72) Inventors: Sungho Jeong, Gwangju (KR); Jeonghwan In, Gwangju (KR); Chan Kyu Kim, Gwangju (KR); Seokhee Lee, Gwangju (KR)

(73) Assignee: GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 0 days.

(21) Appl. No.: 14/104,888

(22) Filed: Dec. 12, 2013

(65) Prior Publication Data

US 2014/0168645 A1  Jun. 19, 2014

(30) Foreign Application Priority Data

Dec. 13, 2012 (KR) .................... 10-2012-0145150

(51) Int. Cl.
*G01N 21/71* (2006.01)
*G01J 3/443* (2006.01)
*G01J 3/28* (2006.01)

(52) U.S. Cl.
CPC .............. *G01N 21/718* (2013.01); *G01J 3/28* (2013.01); *G01J 3/443* (2013.01)

(58) Field of Classification Search
CPC .................................................. G01N 21/718
(Continued)

(56) References Cited

U.S. PATENT DOCUMENTS

| 6,753,957 B1 * | 6/2004 | Graft | G01N 21/718 356/318 |
| 2005/0175507 A1 * | 8/2005 | Tsukruk | B01D 67/0069 422/68.1 |

(Continued)

FOREIGN PATENT DOCUMENTS

| KR | 20050024392 A | 3/2005 |
| KR | 20090082893 A | 7/2009 |

(Continued)

OTHER PUBLICATIONS

Korean Notice of Allowance dated Jun. 11, 2014.

*Primary Examiner* — Tarifur Chowdhury
*Assistant Examiner* — Omar Nixon
(74) *Attorney, Agent, or Firm* — Hauptman Ham, LLP (57) ABSTRACT

Disclosed herein is a quantitative analysis method for measuring a target element in a specimen using laser-induced plasma spectrum. More particularly, the present invention relates to a method for analyzing a composition ratio of a target element by calculating peak intensities when peaks overlap each other in a spectrum, and a method for selecting a peak of a wavelength at which the highest precision and reproducibility are secured through linearity of a correlation plot of the peak intensities and a value by dividing a standard deviation value of calibration curve data (peak intensity ratios) by a slope when an internal standard method is used for quantitative analysis of a target element.

7 Claims, 6 Drawing Sheets

(58) Field of Classification Search
USPC .......................................................... 356/318
See application file for complete search history.

(56) References Cited

U.S. PATENT DOCUMENTS

| | | | |
|---|---|---|---|
| 2006/0054607 A1* | 3/2006 | Wu .................... | B23K 26/0069 |
| | | | 219/121.83 |
| 2012/0029836 A1* | 2/2012 | Hermann ................ | G01J 3/443 |
| | | | 702/28 |
| 2012/0099103 A1* | 4/2012 | Hahn ........................... | 356/316 |
| 2013/0327981 A1* | 12/2013 | Yamada .............. | C01B 31/0446 |
| | | | 252/182.12 |

FOREIGN PATENT DOCUMENTS

| | | |
|---|---|---|
| KR | 20110043209 A | 4/2011 |
| KR | 20110077388 A | 7/2011 |

* cited by examiner

QUANTITATIVE ANALYSIS METHOD FOR MEASURING TARGET ELEMENT IN SPECIMEN USING LASER-INDUCED PLASMA SPECTRUM

CROSS-REFERENCE TO RELATED APPLICATION

This application claims priority to Korean Patent Application No. 10-2012-0145150 filed on 13 Dec. 2012, and all the benefits accruing therefrom under 35 U.S.C. §119, the contents of which is incorporated by reference in its entirety.

BACKGROUND

1. Technical Field

The present invention relates to a quantitative analysis method for measuring a target element in a specimen using a laser-induced plasma spectrum. More particularly, the present invention relates to a method for analyzing a composition ratio of a target element by calculating peak intensities when peaks overlap each other in a spectrum, and a method for selecting a peak of a wavelength at which the highest precision and reproducibility are secured when an internal standard method is used for quantitative analysis of the target element.

2. Description of the Related Art

Since laser-induced plasma emits light of a specific wavelength depending on materials, components of a material can be qualitatively or quantitatively analyzed by collecting the light. Laser-induced breakdown (plasma) spectroscopy (LIBS or LIPS) is one method for analyzing components of a material using collected light based on spectroscopic analysis using plasma, created by inducing breakdown which is a discharge phenomenon using a high power laser, as an excitation source. In plasma induced by a laser, a specimen is vaporized to generate atoms and ions present in an excited state. The atoms and ions in the excited state return to a ground state after a certain lifetime by emitting electromagnetic waves at an intrinsic wavelength depending on the types of elements and excited states. Thus, by analyzing the emitted spectrum of the wavelength, the components of the material can be qualitatively or quantitatively analyzed.

Figure 1:
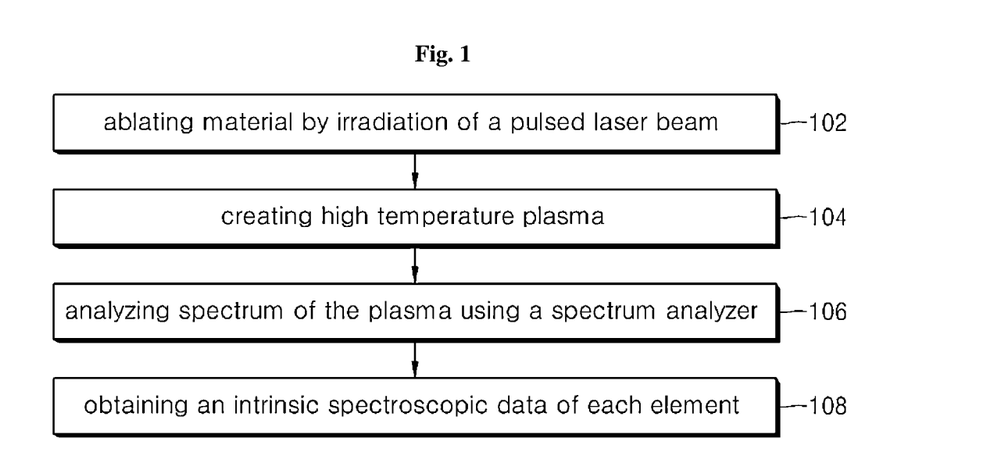
FIG. 1 illustrates an operational principle of LIBS using a typical technique.

FIG. 1 illustrates an operation principle of LIBS using a typical technique.

Referring to FIG. 1, in step 102, when a very small amount (a few μg) of a material is ablated (in which a material is removed through vaporization by a laser beam) upon irradiation of a pulsed laser beam, the ablated material is ionized by absorbing laser energy within an extremely short time (generally, within a few nanoseconds), and then, high-temperature plasma of about 15,000K or more is created in step 104. After irradiation of the pulsed laser beam, each element present in the plasma emits a specific spectrum corresponding thereto while the high-temperature plasma is cooled. Then, the spectrum is collected and analyzed using a spectrum analyzer in step 106, and an intrinsic spectroscopic data of each element is obtained in step 108, so that the composition and amounts of the components of the material can be measured through analysis of these data.

Such an LIBS technique is different from other measurement techniques in terms of: 1) Time for entire measurement is within one second; 2) There is no need for separate sampling and preprocessing for measurement; 3) Since only an infinitesimal amount (a few μg) of a material is used for each measurement, a composition of the material can be measured with nanometer-level precision while the material is ablated in a depth direction; 4) There is no need for separate conditions for measurement and the measurement can be carried out in air; 5) All elements except for inert gas can be analyzed with ppm-level precision; and 6) equipment can be prepared at relatively low costs.

In spectrum analysis by typical LIBS, the intensity of the spectrum is calculated by integrating the spectral line from the baseline. When peaks adjoin each other, peak intensity can be calculated by a curve fitting method. However, when the peaks are too close to each other, there is a problem in that accuracy of a calculated value is deteriorated.

Moreover, in an internal standard method by which components of a specimen to be tested are quantified from the ratio of peak intensities of different elements of the specimen, peaks are typically selected using a limit of detection, a relative standard deviation, and the like. However, the limit of detection is a concept for a material having an extremely low concentration, and when the relative standard deviation is applied to a nonlinear calibration curve (nonlinear calibration curve appears in analysis of an element having a high concentration), an optimal peak cannot be selected.

Therefore, there is a need for a method, by which intensity of the spectrum can be measured even when peaks overlap each other in a spectrum using LIBS, and which can select an optimal spectrum in use of an internal standard method.

BRIEF SUMMARY

It is an aspect of the present invention to provide a method by which intensities of a laser-induced plasma spectrum can be calculated even when peaks of the spectrum very closely overlap each other in laser-induced breakdown (plasma) spectroscopy, and by which a peak having excellent precision and reproducibility can be determined when an analysis target element has a high concentration.

In accordance with one aspect of the present invention, a quantitative analysis method for measuring a target element in a specimen includes: obtaining a spectrum generated from laser-induced plasma upon irradiation of a laser beam to a specimen including a target element; obtaining a fitting curve of a remaining element from the spectrum; obtaining a peak curve of the target element by subtracting the fitting curve of a remaining element from the spectrum; calculating a peak intensity of the peak curve of the target element; and obtaining a composition ratio of the target element based on a ratio of the peak intensity of the peak curve of the target element to the peak intensity of the peak curve of the remaining element.

In addition, to select a peak of a wavelength most suitable for an internal standard method, when a correlation plot of the peak intensity obtained while changing laser energy is a straight line passing through an original point, a wavelength, at which a coefficient of determination $R^2$ is large and a slope change is small with respect to laser energy change, is selected, or after obtaining a calibration curve using the intensity of each peak and a composition ratio of each element, an optimal wavelength can be selected by calculation of $$\frac{\sigma_{R_i}}{S}$$

($\sigma_{R_i}$ is a standard deviation of ratios of the peak intensities and $S$ is a slope of the calibration curve).

As described above, the quantitative analysis method according to embodiments of the invention has advantages in that the peak intensity can be calculated even in the case that accurate analysis is difficult, for example, even when the peaks in a laser-induced plasma spectrum overlap each other, and in that improved results in terms of precision and reproducibility can be obtained through selection of an optimal peak even when a calibration curve is nonlinear due to a high concentration of a target element.

BRIEF DESCRIPTION OF THE DRAWINGS

The above and other aspects, features, and advantages of the present invention will become apparent from the detailed description of the following embodiments in conjunction with the accompanying drawings, in which.

DETAILED DESCRIPTION

Now, exemplary embodiments of the present invention will be described in detail with reference to the accompanying drawings. It should be understood that the present invention is not limited to the following embodiments and may be embodied in different ways, and that the embodiments are given to provide complete disclosure of the invention and to provide thorough understanding of the invention to those skilled in the art. The scope of the invention is limited only by the accompanying claims and equivalents thereof. Like components will be denoted by like reference numerals throughout the specification.

1. Calculation of Peak Intensity at Specific Wavelength

According to one exemplary embodiment of the invention, a quantitative analysis method for measuring a target element in a specimen includes: obtaining a spectrum generated from laser-induced plasma upon irradiation of a laser beam to a specimen including a target element; obtaining a fitting curve of a remaining element from the spectrum; obtaining a peak curve of the target element by subtracting the fitting curve of a remaining element from the spectrum; calculating a peak intensity of the peak curve of the target element; and obtaining a composition ratio of the target element based on a ratio of the peak intensity of the peak curve of the target element to the peak intensity of the peak curve of the remaining element.

First, when the specimen including a standard element is irradiated with a laser beam, plasma is generated from the specimen. Particularly, the irradiating laser beam is desirably appropriately selected so that ablation of the specimen can be easily performed depending on the material of the specimen and a chemical composition thereof.

Spectral components of plasma are shown as a spectrum by a spectral detection optical unit and the like.

Figure 2A:
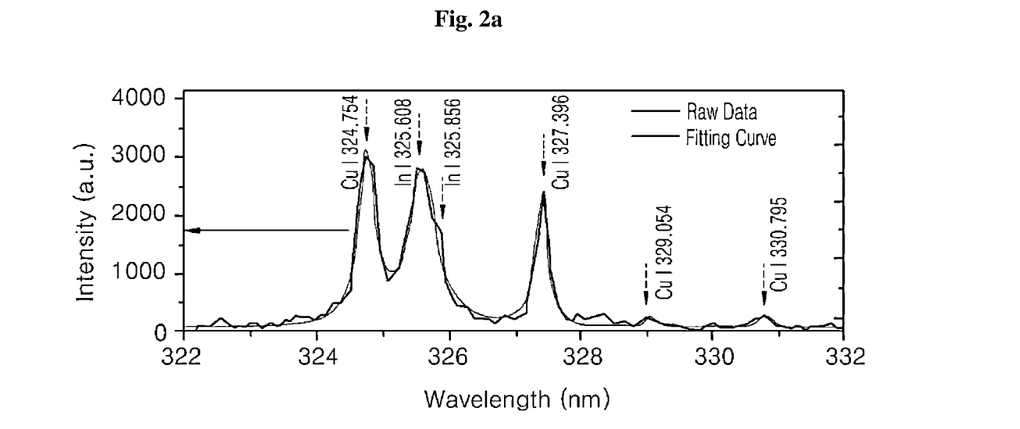
FIGS. 2a and 2b show one example of a laser-induced plasma spectrum.
Figure 2B:
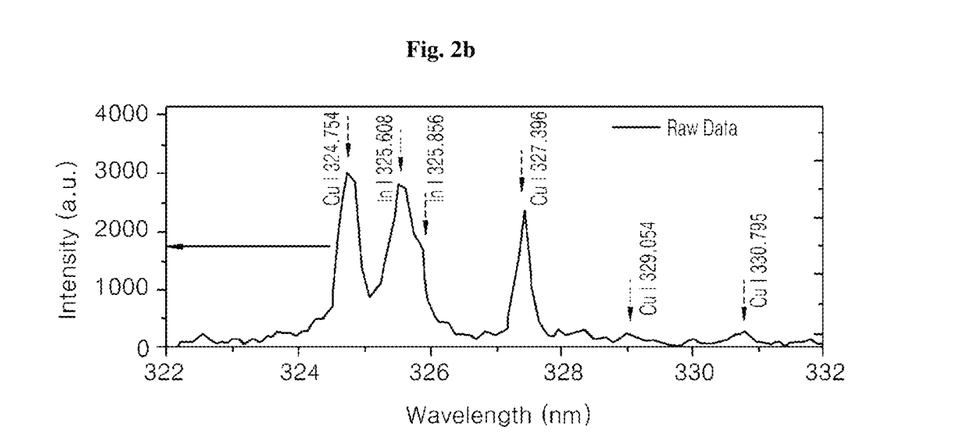

One example of the obtained spectrum is shown in FIGS. 2a and 2b.

In the spectrum, although peaks of In, a target element, appear at wavelengths of 325.608 nm and 325.856 nm, the peaks overlap each other and thus are not individually distinguished from each other. In this case, when intensities of the individual peaks are obtained by a curve fitting method, calculation time is too long, or calculation errors such as incorrect values, and the like, frequently occur. In addition, since shapes of the peaks are distorted, it is difficult to obtain the accurate peak intensities when the peaks are considered to be one peak. In addition, since the peaks partially overlap neighboring peaks of Cu, a remaining element, it is difficult to obtain accurate peak intensities despite integration from a baseline.

To solve these problems, embodiments of the present invention provide a novel method for obtaining an intensity of a peak of a target element.

First, a fitting curve of a remaining element is obtained from a spectrum using a curve fitting method. The fitting curve may be formed through the Lorentzian function. A transformation equation for peak fitting is represented by Equation 1:

$$y = \frac{1}{\pi} \sum_i \left( A_i \frac{\gamma_i}{(x - x_i)^2 + \gamma_i^2} \right) + ax + b,$$

wherein $A_i$ is peak intensity.

Here, a fitting curve of a remaining element is obtained from the spectrum. In FIG. 2a, although the fitting curve may be obtained using each of In peaks at 325.608 nm and at 325.856 nm as an individual peak, calculation errors can be reduced when the fitting curve is obtained by combining the two peaks into one peak.

In addition, a peak curve of a target element may be obtained by subtracting the Cu fitting curve from the spectrum.

Figure 3:
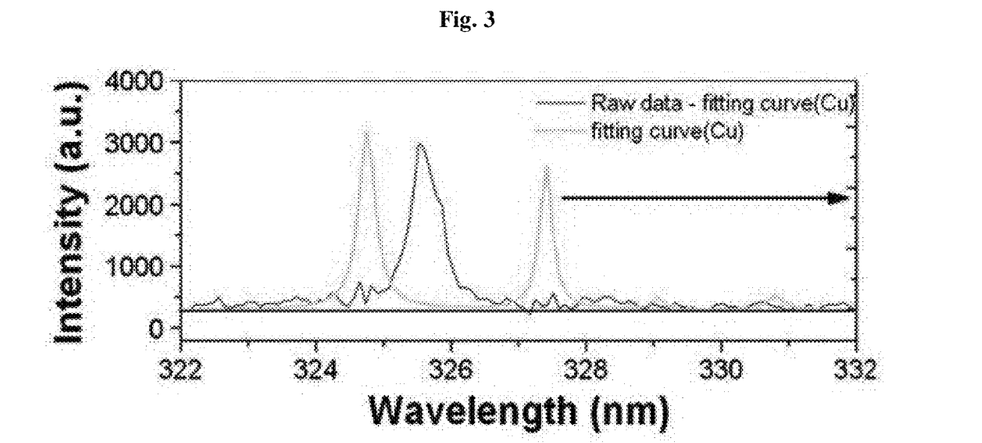
FIG. 3 separately shows a Cu fitting curve obtained from the laser-induced plasma spectrum by a curve fitting method and an In peak curve obtained by subtracting the Cu fitting curve from the spectrum.

The peak curve of a target element and the Cu fitting curve obtained through the above process are shown in FIG. 3. In FIG. 3, "Raw data-fitting curve (Cu)" corresponds to the peak curve of a target element, In.

By integrating the peak curve of target element from the baseline, a combined intensity of the In peaks at 325.608 nm and at 325.856 nm may be calculated, and this value may be used in calculation of ratios of peak intensities.

When another small peak overlaps one side of one peak in a spectrum, the peak intensities may be estimated using the curve fitting method excluding data of the small peak overlapped on the side of a large peak.

2. Selection of Optimal Peak—Correlation Plot

To measure a composition ratio of a target element in a specimen by an internal standard method, two specific peaks of different elements must be selected in the spectrum. Here, the two specific peaks must have an unchanged ratio of peak intensities even though other conditions are changed.

In this invention, to select the specific peaks, a correlation plot may be analyzed while changing laser energy. Although the laser energy is not particularly limited, it is advantageous that the laser energy is changed within a range from 2 J/cm² to 24 J/cm².

When the correlation plot between intensities of the specific peaks is curve-fitted to a straight line-shaped graph passing through the origin, two peaks exhibiting a high coefficient of determination R² are selected. Preferably, the peaks exhibiting the highest coefficient of determination approaching 1 are selected as the specific peak. The coefficient of determination R² may be calculated by Equation 2:

$$R^2 = 1 - \frac{\sum_i (y_i - f_i)^2}{\sum_i (y_i - \bar{y})^2}$$

wherein $y_i$ is a measured intensity and $f_i$ is a function value of a fitting curve.

In addition, a slope change of a fitted straight line depending on the laser energy may be calculated, and a peak exhibiting the smallest slope change is selected as the other specific peak. The slope change may be calculated by Equation 3:

$$\text{Slope change (\%)} = \frac{\text{Maximum slope} - \text{Minimum slope}}{\text{Maximum slope}} \times 100.$$

Finally, from the specific peaks selected through the above process, the fitted straight line of the correlation plot is obtained and a slope of the fitted straight line is calculated. Then, the slope may be associated with the composition ratio of the element. As a result, by comparing the slope of the fitted straight line of the correlation plot of the intensities of the selected specific peaks of the specimen with the slope of the fitted straight line of the correlation plot of a material, the composition ratio of which is known, quantitative analysis of the target element is possible.

3. Selection of Optimal Peak—Calibration Curve

To select the specific peak, a calibration curve showing a relationship between the composition ratio of the element of the material known in advance and the ratio of the peak intensities may be used. In the calibration curve, peaks exhibiting small values of $$\frac{\sigma_{R_i}}{S}$$

($\sigma_{R_i}$ is a standard deviation of ratios of the peak intensities and S is a slope of the calibration curve) may be selected as the specific peaks for confirmation of the composition ratio of the target element.

$$\frac{\sigma_{R_i}}{S}$$

may be calculated by Equation 4:

$$\frac{\sigma_{R_i}}{S} = \sigma_{R_i} \times \frac{\Delta R_c}{\Delta R_i},$$

wherein $\Delta R_i$ is a difference of peak intensity ratios from a neighboring sample, and $\Delta R_c$ is a difference of composition ratios from the neighboring sample.

As this value is smaller, precision of a measurement is increased, so that desired precision can be obtained despite the small number of repeated measurements.

Finally, by selecting the peaks exhibiting small values of $$\frac{\sigma_{R_i}}{S},$$

the calibration curve between the composition ratio of the target element and the peak intensity ratio of the selected peaks is derived, and the peak intensity ratio of the specimen is substituted into the calibration curve, so that the composition ratio of the target element in the specimen can be calculated.

Now, the quantitative analysis method will be described in more detail with reference to some examples.

Example 1

Selection of Optimal Peak by Correlation Plot

Plasma was generated by irradiating specimens having ratios of In to Cu (In/Cu), which were respectively 0.726, 0.666, 0.534 and 0.492 through X-ray fluorescence analysis, with a laser energy beam while changing laser energy, and spectra generated from the plasma were obtained.

In addition, as described above, a Cu peak fitting curve and an In peak curve were individually obtained from overlapping peaks, and each of peak intensities was calculated.

Then, after a correlation plot between Cu and In peak intensities was obtained and adjusted to coincide with a straight line passing through an origin point, a coefficient of determination R², a slope of the straight line, and a slope change depending on laser energy change (refer to Equation 3) were calculated. Calculated results are shown in Table 1.

TABLE 1

| In/Cu ratio by XRF | Cu wavelength (nm) | In wavelength (nm) | R² | Slope | Slope change (%) |
|---|---|---|---|---|---|
| In/Cu = 0.726 | 219.975 | 303.935 | 0.926 | 2.771 | 14.0 |
| | 219.975 | 410.175 | 0.927 | 1.732 | 11.8 |
| | 229.384 | 410.175 | 0.866 | 3.935 | 8.8 |
| | 324.754 | 325.608 | 0.988 | 1.570 | 4.2 |
| | 327.396 | 325.608 | 0.989 | 2.548 | 2.6 |
| | 330.795 | 325.608 | 0.927 | 21.703 | 5.0 |
| In/Cu = 0.660 | 217.894 | 410.175 | 0.853 | 2.691 | 15.1 |
| | 217.894 | 451.130 | 0.858 | 4.337 | 5.9 |
| | 219.975 | 303.935 | 0.891 | 2.529 | 12.9 |
| | 324.754 | 325.608 | 0.985 | 1.395 | 5.9 |
| | 327.396 | 325.608 | 0.984 | 2.275 | 4.7 |
| In/Cu = 0.534 | 324.754 | 325.608 | 0.964 | 1.089 | 7.7 |
| | 327.396 | 325.608 | 0.962 | 1.787 | 5.1 |
| In/Cu = 0.492 | 217.894 | 410.175 | 0.897 | 1.627 | 5.4 |
| | 219.227 | 410.175 | 0.859 | 1.340 | 9.7 |
| | 219.975 | 410.175 | 0.897 | 1.012 | 9.5 |
| | 224.700 | 410.175 | 0.869 | 1.078 | 7.8 |
| | 324.754 | 325.608 | 0.972 | 1.055 | 2.7 |
| | 327.396 | 325.608 | 0.968 | 1.752 | 3.4 |

In Table 1, it can be seen that, even though the composition ratio of Cu and In was changed, the coefficient of determination R² had the largest value approaching 1 in the correlation plot of peaks at 324.754 nm for Cu and at 325.608 nm for In. In addition, the slope change was relatively small in the correlation plot of peaks at 324.754 nm for Cu and at 325.608 nm for In.

Figure 4:
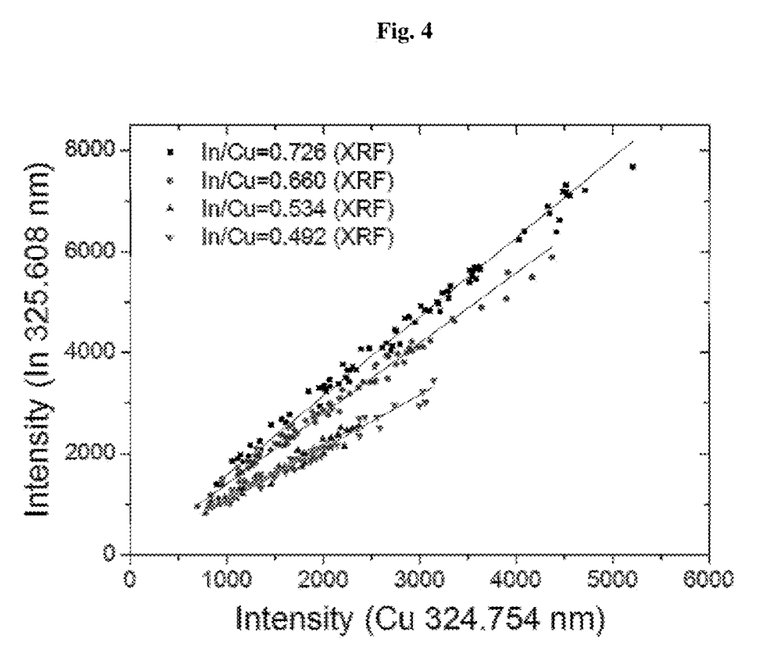
FIG. 4 is a correlation plot of peak intensities at selected Cu and In wavelengths (Cu: 324.754 nm, In: 325.608 nm) using the peak intensities calculated by the above method.

The correlation plot of the peak intensities at the selected Cu and In wavelengths (Cu 324.754 nm, In 325.608 nm) is shown in FIG. 4.

Therefore, it could be seen that the peaks exhibiting a consistent intensity ratio which is not changed due to variation of laser energy conditions could be selected through calculation using the correlation plot.

Example 2

Selection of Optimal Peak by Calibration Curve

Plasma was generated by irradiating specimens having ratios of In to Cu (In/Cu), which were respectively 0.726, 0.666 and 0.534 through X-ray fluorescence analysis, with a laser beam while changing laser energy, and spectra generated from the plasma were obtained.

In addition, as described above, a Cu peak fitting curve and an In peak curve were individually obtained from overlapping peaks, and each peak intensity was calculated.

Values of $$\frac{\sigma_{R_i}}{S}$$

were calculated from a calibration curve showing relation between the ratio of In to Cu (In/Cu) confirmed through X-ray fluorescence analysis and the peak intensity ratio calculated from the In and Cu curves as shown in Table 2.

$$\frac{\sigma_{R_i}}{S}.$$

Example 3

Correlation Plot Depending on Peak Intensity of Optimal Wavelength

To confirm consistency of the correlation plot, spot sizes or stage positions were adjusted. As the spot sizes or stage positions are adjusted, energy density varies.

Figure 6A:
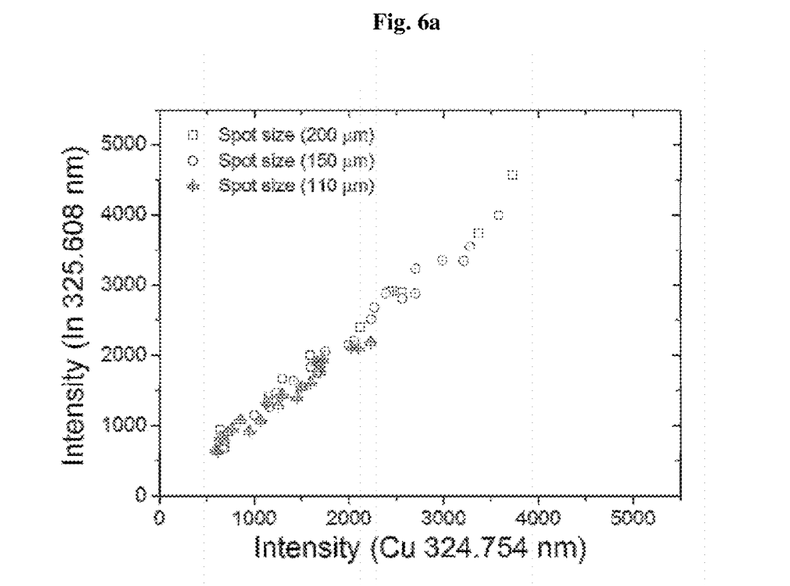
FIGS. 6a and 6b are correlation plots of the peak intensities at the Cu and In wavelengths (Cu: 324.754 nm, In: 325.608 nm), consistency of which is confirmed while adjusting spot sizes or stage positions.
Figure 6B:
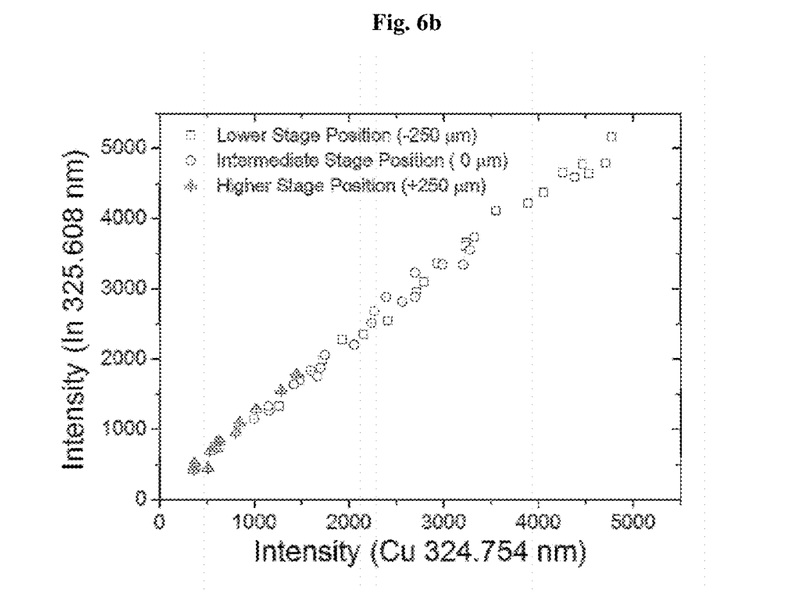

FIGS. 6a and 6b shows correlation plots of peak intensities at selected optimal wavelengths (Cu: 324.754 nm, In: 325.608 nm), and it can be seen that the peak intensity ratio is not affected by experimental variables such as energy densities, and the like.

Figure 7A:
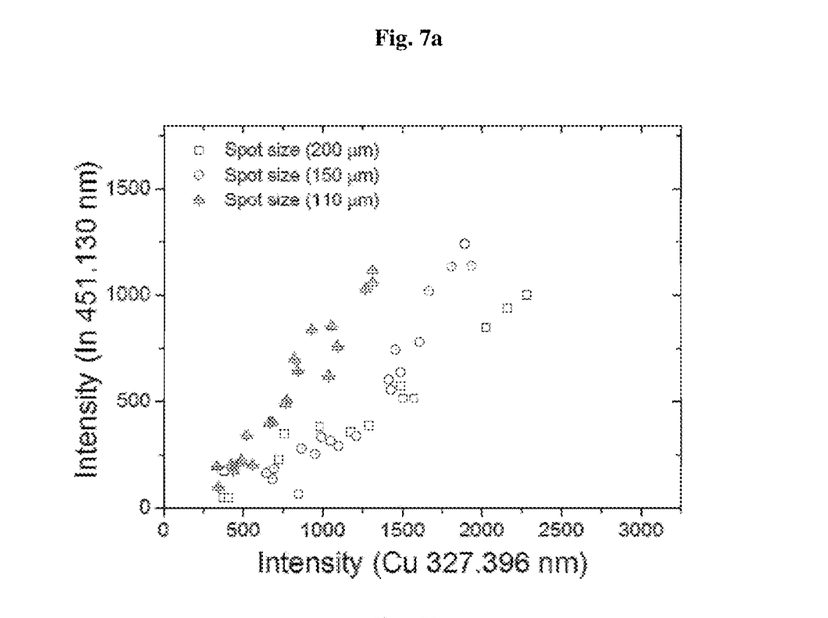
FIGS. 7a and 7b are correlation plots of the peak intensities at the Cu and In wavelengths (Cu: 327.396 nm, In: 451.608 nm) when spot sizes or stage positions are adjusted.
Figure 7B:
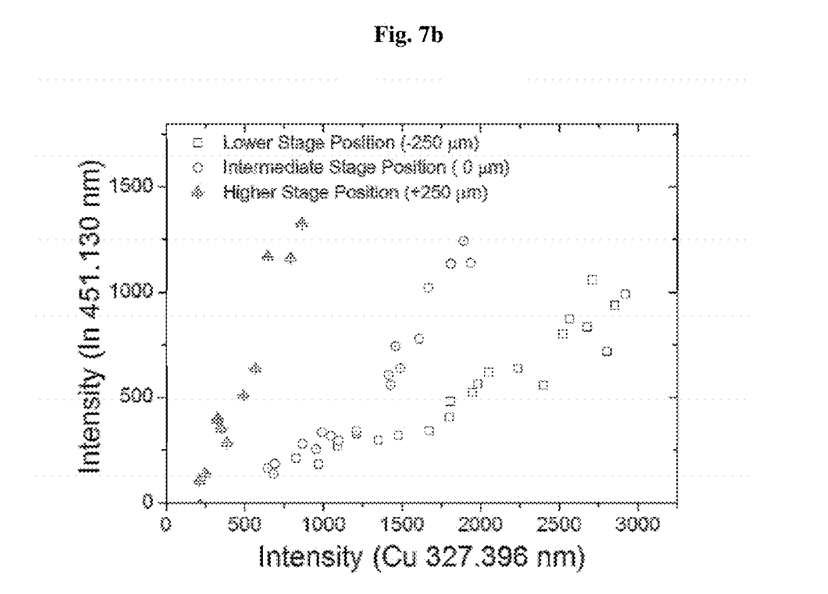

FIGS. 7a and 7b shows correlation plots of peak intensities at random wavelengths (Cu: 327.396 nm, In: 451.608 nm), and it can be seen that the peak intensity ratio is greatly affected by the experimental variables such as energy densities, and the like.

Therefore, at the selected optimal wavelengths, constant results can be derived despite differences of the experimental variables, and reproducibility of composition analysis can be improved.

Although the present invention has been described with reference to some embodiments in conjunction with the accompanying drawings, it should be understood that the present invention is not limited to the embodiments and may be embodied in different ways, and that various modifica-

TABLE 2

| | | | $\frac{\sigma_{R_i}}{S}$ | | |
|---|---|---|---|---|---|
| Laser energy | Cu wavelength (nm) | In wavelength (nm) | $\sigma_{R_i}$ (In/Cu = 0.726) $\Delta R_c = 0.066$ | $\sigma_{R_i}$ (In/Cu = 0.660) $\Delta R_c = 0.126$ | $\sigma_{R_i}$ (In/Cu = 0.534) $\Delta R_c = 0.042$ |
| 1.56 mJ (8.80 J/cm$^2$) | 213.598 | 303.935 | 0.0344 | 0.0806 | 0.0490 |
| | 217.894 | 303.935 | 0.0508 | 0.0736 | 0.0562 |
| | 224.700 | 303.935 | 0.0388 | 0.0568 | 0.0769 |
| | 224.700 | 410.175 | 0.0859 | 0.0356 | 0.0599 |
| | 324.754 | 325.608 | 0.0169 | 0.0297 | 0.0460 |
| 1.77 mJ (10.01 J/cm$^2$) | 211.210 | 410.175 | 0.0880 | 0.0653 | 0.0815 |
| | 219.227 | 303.935 | 0.0732 | 0.0653 | 0.0783 |
| | 221.811 | 410.175 | 0.0889 | 0.0362 | 0.0824 |
| | 224.261 | 303.935 | 0.0624 | 0.0570 | 0.0821 |
| | 324.754 | 325.608 | 0.0121 | 0.0238 | 0.0571 |
| | 327.396 | 325.608 | 0.0140 | 0.0261 | 0.0831 |

In FIG. 2, it could be seen that the values of $$\frac{\sigma_{R_i}}{S}$$

of the calibration curve for the peak intensity ratios at 324.754 nm for Cu and at 325.608 nm for In were the smallest.

Figure 5:
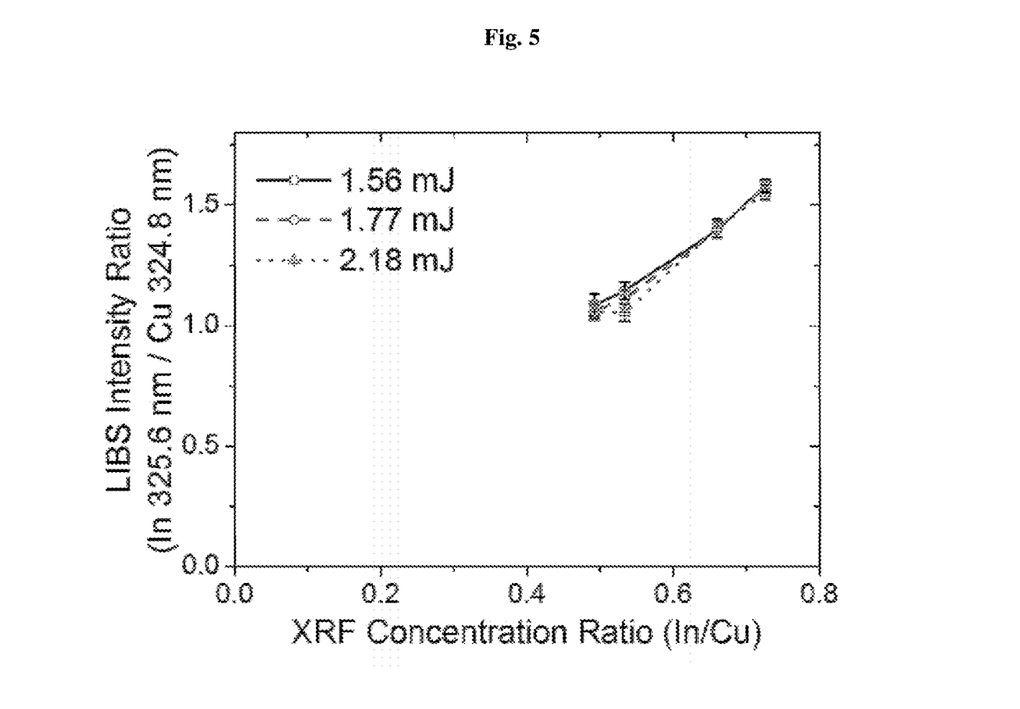
FIG. 5 is a calibration curve for ratios of the peak intensities at the selected Cu and In wavelengths (Cu: 324.754 nm, In: 325.608 nm)

The calibration curve for the peak intensity ratios at the selected Cu and In wavelengths (Cu: 324.754 nm, In: 325.608 nm) is shown in FIG. 5.

Therefore, it can be seen that a calibration curve with excellent precision could be selected from the values of tions, changes, alterations, and equivalent embodiments can be made by those skilled in the art without departing from the spirit and scope of the invention. Therefore, it should be understood that the foregoing embodiments are provided for illustration only and are not to be in any way construed as limiting the present invention.

What is claimed is:

1. A quantitative analysis method for measuring a target element in a specimen, comprising:
    obtaining a spectrum generated from laser-induced plasma upon irradiation of a laser beam to a specimen including a target element;
    obtaining a fitting curve of a remaining element from the spectrum using Lorentzian function as a curve fitting method;

obtaining a peak curve of the target element by subtracting the fitting curve of a remaining element from the spectrum;

calculating a peak intensity of the peak curve of the target element and a peak intensity of the fitting curve of a remaining element; and obtaining a composition ratio of the target element based on a ratio of the peak intensity of the peak curve of the target element to the peak intensity of the fitting curve of the remaining element, wherein, when the correlation plot is represented by a straight line passing through the origin, the selected wavelengths are wavelengths at which a slope change is small with respect to laser energy change.

2. The quantitative analysis method according to claim 1, wherein the composition ratio of the target element is measured by applying peak intensities at wavelengths, selected by analyzing a correlation plot of peak intensities obtained by changing laser energy, to an internal standard method.

3. The quantitative analysis method according to claim 2, wherein, when the correlation plot is represented by a straight line passing through the origin, the selected wavelengths are wavelengths at which a coefficient of determination $R^2$ is large.

4. The quantitative analysis method according to claim 2, wherein, when the correlation plot obtained from the peak intensities at the selected wavelengths is represented by a straight line passing through the origin, a slope of the straight line is compared with a slope of a fitted straight line of a correlation plot of a material, the composition ratio of the target element of which is known in advance.

5. The quantitative analysis method according to claim 1, wherein the obtaining a composition ratio of the target element comprises:

obtaining a calibration curve using each peak intensity ratio and a composition ratio of each element;

calculating values of $$\frac{\sigma_{R_i}}{S}$$

($\sigma_{R_i}$ is a standard deviation of ratios of the peak intensities, and S is a slope of the calibration curve) from the calibration curve; and selecting peaks at wavelengths at which the values of $$\frac{\sigma_{R_i}}{S}$$

are small, and measuring the composition ratio of the target element by applying the intensities of the selected peaks to an internal standard method.

6. The quantitative analysis method according to claim 5, wherein ratios of peak intensities at the selected wavelengths are substituted into the calibration curve to obtain the composition ratio of the target element.

7. The quantitative analysis method according to claim 1, wherein a transformation equation for peak fitting is represented by Equation 1:

$$y = \frac{1}{\pi} \sum_i \left( A_i \frac{\gamma_i}{(x-x_i)^2 + \gamma_i^2} \right) + ax + b,$$

wherein $A_i$ is peak intensity.

* * * * *